United States Patent
Balzano et al.

(10) Patent No.: US 11,432,858 B2
(45) Date of Patent: *Sep. 6, 2022

(54) STABILIZER HOLDER AND INSERTER TOOL AND METHODS

(71) Applicant: Zimmer Biomet CMF and Thoracic, LLC, Jacksonville, FL (US)

(72) Inventors: Isabella Balzano, New Albany, OH (US); Saddy Garcia, St. Augustine, FL (US); Jayden Garfield, Jacksonville, FL (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 163 days.

This patent is subject to a terminal disclaimer.

(21) Appl. No.: 16/908,188

(22) Filed: Jun. 22, 2020

(65) Prior Publication Data
US 2020/0315676 A1    Oct. 8, 2020

Related U.S. Application Data

(63) Continuation of application No. 15/892,926, filed on Feb. 9, 2018, now Pat. No. 10,722,279.
(Continued)

(51) Int. Cl.
*A61B 17/58*    (2006.01)
*A61B 17/80*    (2006.01)
(Continued)

(52) U.S. Cl.
CPC ........ *A61B 17/8076* (2013.01); *A61B 17/808* (2013.01); *A61B 17/8019* (2013.01);
(Continued)

(58) Field of Classification Search
CPC ............ A61B 17/8076; A61B 17/8019; A61B 17/808; A61B 17/8875; A61B 17/80; A61F 2/28; A61F 2002/30482; A61F 2002/4622
(Continued)

(56) References Cited

U.S. PATENT DOCUMENTS

| 212,242 A | 2/1879 | Loper |
| 2,616,328 A | 11/1952 | Kingsmore |

(Continued)

FOREIGN PATENT DOCUMENTS

| CN | 101123922 A | 2/2008 |
| CN | 201930064 U | 8/2011 |

(Continued)

OTHER PUBLICATIONS

U.S. Appl. No. 15/893,271, filed Feb. 9, 2018, Pectus Bar and Stabilizer Devices and Methods.
(Continued)

*Primary Examiner* — Jessica Weiss
(74) *Attorney, Agent, or Firm* — Schwegman Lundberg & Woessner, P.A.

(57) ABSTRACT

A pectus bar stabilizer insertion tool can include a first handle, a second handle, a first head, a second head, and a locking shaft. The first handle can include a first distal portion. The second handle can include a second distal portion, and the second handle can be pivotably coupled to the first handle. The first and second handles can be moveable between an open position and a closed position. The first head can be coupled to the first distal portion and can be engageable with a first portion of a stabilizer. The first head can include a driver engageable with a lock of the stabilizer. The second head can be coupled to the second distal portion and can be engageable with a second portion
(Continued)

of the stabilizer. The locking shaft can be coupled to the driver and operable to lock and unlock the stabilizer to a pectus bar.

20 Claims, 6 Drawing Sheets

Related U.S. Application Data (60) Provisional application No. 62/483,494, filed on Apr. 10, 2017, provisional application No. 62/457,532, filed on Feb. 10, 2017.

(51) Int. Cl.
*A61F 2/28* (2006.01)
*A61B 17/88* (2006.01)
*A61F 2/30* (2006.01)
*A61F 2/46* (2006.01)

(52) U.S. Cl.
CPC ............ *A61B 17/8875* (2013.01); *A61F 2/28* (2013.01); *A61F 2002/30482* (2013.01); *A61F 2002/4622* (2013.01)

(58) Field of Classification Search
USPC .. 606/99–100, 901, 905, 205–209, 191, 198
See application file for complete search history.

(56) References Cited

U.S. PATENT DOCUMENTS

| | | |
|---|---|---|
| 3,946,728 A | 3/1976 | Bettex |
| 4,082,332 A | 4/1978 | Palmer |
| 4,201,215 A | 5/1980 | Crossett et al. |
| 4,202,327 A | 5/1980 | Glancy |
| 4,327,715 A | 5/1982 | Corvisier |
| 5,092,889 A | 3/1992 | Campbell, Jr. |
| 5,605,364 A | 2/1997 | Shelledy |
| 5,755,808 A | 5/1998 | Decarlo et al. |
| 6,005,018 A | 12/1999 | Cicierega et al. |
| 6,007,538 A | 12/1999 | Levin |
| 6,024,759 A | 2/2000 | Nuss et al. |
| 6,139,550 A | 10/2000 | Michelson |
| 6,306,136 B1 | 10/2001 | Baccelli |
| 6,355,038 B1 | 3/2002 | Pisharodi |
| 6,656,179 B1 | 12/2003 | Schaefer et al. |
| 6,689,134 B2 | 2/2004 | Ralph et al. |
| 6,872,210 B2 | 3/2005 | Hearn |
| 7,156,847 B2 | 1/2007 | Abramson |
| 7,601,165 B2 | 10/2009 | Stone |
| 8,597,327 B2 | 12/2013 | Stone et al. |
| 8,715,285 B2 | 5/2014 | Lewis et al. |
| 8,876,823 B2 | 11/2014 | Li et al. |
| 9,138,272 B2 | 9/2015 | Roman et al. |
| 9,339,388 B2 | 5/2016 | Dartevelle |
| 9,668,792 B2 | 6/2017 | Roman et al. |
| 9,743,968 B2 | 8/2017 | Litch et al. |
| 9,775,657 B2 | 10/2017 | Bernstein et al. |
| 9,833,269 B2 | 12/2017 | Park |
| 9,872,708 B2 | 1/2018 | Park |
| 10,058,364 B2 | 8/2018 | Garcia |
| 10,617,455 B2 | 4/2020 | Maxson |
| 10,722,279 B2 | 7/2020 | Balzano et al. |
| 10,820,931 B2 | 11/2020 | Garcia et al. |
| 2002/0143336 A1 | 10/2002 | Hearn |
| 2003/0225409 A1 | 12/2003 | Freid et al. |
| 2004/0030338 A1 | 2/2004 | Paul |
| 2004/0116931 A1 | 6/2004 | Carlson |
| 2004/0117016 A1* | 6/2004 | Abramson ......... A61B 17/8076 606/71 |
| 2004/0204713 A1 | 10/2004 | Abdou |
| 2005/0049595 A1 | 3/2005 | Suh et al. |
| 2006/0058786 A1* | 3/2006 | Kim ................. A61B 17/8076 606/60 |
| 2006/0089648 A1 | 4/2006 | Masini |
| 2006/0259141 A1* | 11/2006 | Roman .............. A61B 17/8061 623/11.11 |
| 2006/0276794 A1 | 12/2006 | Stern |
| 2008/0082101 A1 | 4/2008 | Reisberg |
| 2008/0097444 A1 | 4/2008 | Erickson et al. |
| 2008/0262549 A1 | 10/2008 | Bennett et al. |
| 2009/0062918 A1* | 3/2009 | Wang ................. A61B 17/7062 604/218 |
| 2010/0256691 A1 | 10/2010 | Park |
| 2011/0160776 A1 | 6/2011 | Erickson et al. |
| 2011/0251540 A1 | 10/2011 | Notrica |
| 2012/0130371 A1 | 5/2012 | Li et al. |
| 2012/0303121 A1 | 11/2012 | Douget et al. |
| 2013/0165934 A1* | 6/2013 | Ibrahim ............ A61B 17/8004 606/71 |
| 2013/0204310 A1 | 8/2013 | Roman et al. |
| 2014/0117016 A1 | 5/2014 | Hodge |
| 2014/0135853 A1 | 5/2014 | Reisberg |
| 2014/0163691 A1 | 6/2014 | Dartevelle |
| 2014/0214103 A1 | 7/2014 | Roman et al. |
| 2014/0309699 A1 | 10/2014 | Houff |
| 2014/0378976 A1 | 12/2014 | Garcia |
| 2015/0038969 A1 | 2/2015 | Garcia et al. |
| 2015/0045794 A1 | 2/2015 | Garcia et al. |
| 2015/0119887 A1 | 4/2015 | May et al. |
| 2015/0134009 A1 | 5/2015 | Licht et al. |
| 2015/0238237 A1 | 8/2015 | Madjarov |
| 2016/0074078 A1 | 3/2016 | Roman et al. |
| 2016/0296262 A1 | 10/2016 | Garcia et al. |
| 2016/0310180 A1 | 10/2016 | Prybis et al. |
| 2016/0367301 A1 | 12/2016 | Madjarov |
| 2017/0156759 A1 | 6/2017 | Park |
| 2017/0215930 A1 | 8/2017 | Lauf et al. |
| 2017/0238981 A1 | 8/2017 | Madjarov et al. |
| 2018/0228523 A1 | 8/2018 | Balzano et al. |
| 2018/0228524 A1 | 8/2018 | Garcia et al. |
| 2018/0256227 A1 | 9/2018 | Maxson |
| 2018/0303527 A1 | 10/2018 | Su |
| 2018/0310973 A1 | 11/2018 | Son et al. |
| 2018/0368896 A1 | 12/2018 | Powell |
| 2019/0046251 A1 | 2/2019 | Detweiler et al. |
| 2019/0059964 A1 | 2/2019 | Notrica |
| 2019/0069938 A1 | 3/2019 | Martinez-Ferro et al. |
| 2019/0314072 A1 | 10/2019 | Uemura et al. |
| 2020/0197058 A1 | 6/2020 | Maxson |
| 2021/0007785 A1 | 1/2021 | Garcia et al. |

FOREIGN PATENT DOCUMENTS

| | | |
|---|---|---|
| CN | 203059880 U | 7/2013 |
| CN | 103767778 A | 5/2014 |
| CN | 104856748 A | 8/2015 |
| CN | 204683752 U | 10/2015 |
| CN | 110325135 A | 10/2019 |
| CN | 110366391 A | 10/2019 |
| EP | 0583520 A1 | 2/1994 |
| EP | 1721580 A1 | 11/2006 |
| JP | 2000501624 A | 2/2000 |
| JP | 2016168086 A | 9/2016 |
| JP | 2020508102 A | 3/2020 |
| JP | 2020509827 A | 4/2020 |
| WO | WO-2004028412 A1 | 4/2004 |
| WO | WO-2013003719 A1 | 1/2013 |
| WO | WO-2015003061 A1 | 1/2015 |
| WO | WO-2015056204 A1 | 4/2015 |
| WO | WO-2015142588 A2 | 9/2015 |
| WO | WO-2017023147 A1 | 2/2017 |
| WO | WO-2017157802 A1 | 9/2017 |
| WO | WO-2018148521 A1 | 8/2018 |
| WO | WO-2018148572 A1 | 8/2018 |
| WO | WO-2018164808 A1 | 9/2018 |

OTHER PUBLICATIONS

U.S. Appl. No. 15/892,926, filed Feb. 9, 2018, Stabilizer Holder and Inserter Tool and Methods.

(56) References Cited

OTHER PUBLICATIONS

U.S. Appl. No. 15/892,847 U.S. Pat. No. 10,617,455, filed Feb. 9, 2018, Pectus Bar Support Devices and Methods.
U.S. Appl. No. 16/804,325, filed Feb. 28, 2020, Pectus Bar Support Devices and Methods.
U.S. Appl. No. 11/402,319, filed Apr. 11, 2006, Pectus Bar Stabilizer.
U.S. Appl. No. 13/662,975 U.S. Pat. No. 8,715,285, filed Oct. 29, 2012, Pectus Bar Stabilizer.
U.S. Appl. No. 14/243,246 U.S. Pat. No. 9,138,272, filed Apr. 2, 2014, Pectus Bar Stabilizer.
U.S. Appl. No. 14/857,422 U.S. Pat. No. 9,668,792, filed Sep. 17, 2015, Pectus Bar Stabilizer.
"U.S. Appl. No. 11/402,319, Advisory Action dated Oct. 13, 2009", 4 pgs.
"U.S. Appl. No. 11/402,319, Appeal Brief filed Jan. 4, 2010", 24 pgs.
"U.S. Appl. No. 11/402,319, Decision on Appeal dated Aug. 29, 2012", 9 pgs.
"U.S. Appl. No. 11/402,319, Examiner Interview Summary dated Apr. 6, 2009", 2 pgs.
"U.S. Appl. No. 11/402,319, Final Office Action dated Aug. 5, 2009", 11 pgs.
"U.S. Appl. No. 11/402,319, Non Final Office Action dated Feb. 23, 2009", 10 pgs.
"U.S. Appl. No. 11/402,319, Reply Brief filed Apr. 26, 2010", 6 pgs.
"U.S. Appl. No. 11/402,319, Reply Brief filed Jun. 2, 2010", 6 pgs.
"U.S. Appl. No. 11/402,319, Response filed Jan. 27, 2009 to Restriction Requirement dated Dec. 31, 2008", 3 pgs.
"U.S. Appl. No. 11/402,319, Response filed Apr. 8, 2009 to Non Final Office Action dated Feb. 23, 2009", 11 pgs.
"U.S. Appl. No. 11/402,319, Response filed Sep. 24, 2009 to Final Office Action dated Aug. 5, 2009", 7 pgs.
"U.S. Appl. No. 11/402,319, Restriction Requirement dated Dec. 31, 2008", 9 pgs.
"U.S. Appl. No. 13/662,975, Notice of Allowance dated Dec. 24, 2013", 9 pgs.
"U.S. Appl. No. 13/662,975, Preliminary Amendment filed Jul. 1, 2013", 11 pgs.
"U.S. Appl. No. 13/662,975, Response filed Sep. 30, 2013 to Restriction Requirement dated Aug. 28, 2013", 9 pgs.
"U.S. Appl. No. 13/662,975, Restriction Requirement dated Aug. 28, 2013", 9 pgs.
"U.S. Appl. No. 14/243,246, Notice of Allowance dated May 20, 2015", 9 pgs.
"U.S. Appl. No. 14/531,US4, Response filed Jan. 12, 2017 to Final Office Action dated Dec. 7, 2016", 9 pgs.
"U.S. Appl. No. 14/857,422, Final Office Action dated Dec. 7, 2016", 12 pgs.
"U.S. Appl. No. 14/857,422, Non Final Office Action dated Apr. 19, 2016", 5 pgs.
"U.S. Appl. No. 14/857,422, Notice of Allowance dated Jan. 25, 2017", 7 pgs.
"U.S. Appl. No. 14/857,422, Response filed Sep. 19, 2016 to Non Final Office Action dated Apr. 19, 2016", 8 pgs.
"U.S. Appl. No. 15/892,847, Notice of Allowance dated Nov. 29, 2019", 10 pgs.
"U.S. Appl. No. 15/892,926, Non Final Office Action dated Nov. 29, 2019", 15 pgs.
"U.S. Appl. No. 15/892,926, Notice of Allowance dated Mar. 23, 2020", 11 pgs.
"U.S. Appl. No. 15/892,926, Response filed Feb. 19, 2020 to Non Final Office Action dated Nov. 29, 2019", 11 pgs.
"U.S. Appl. No. 15/893,271, Non Final Office Action dated Dec. 27, 2019", 12 pgs.
"U.S. Appl. No. 15/893,271, Response filed Mar. 18, 2020 to Non Final Office Action dated Dec. 27, 2019", 13 pgs.
"U.S. Appl. No. 16/804,325, Preliminary Amendment filed Mar. 27, 2020", 6 pgs.
"Australian Application Serial No. 2018217805, First Examination Report dated Nov. 25, 2019", 4 pgs.
"Australian Application Serial No. 2018217805, Response filed Feb. 25, 2020 First Examination Report dated Nov. 25, 2019", 25 pgs.
"Australian Application Serial No. 2018230818, First Examination Report dated Feb. 19, 2020", 5 pgs.
"Australian Application Serial No. 2018230818, Response filed May 5, 2020 to First Examination Report dated Feb. 19, 2020", 23 pgs.
"Australian Application Serial No. 2018230818, Subsequent Examiners Report dated May 28, 2020", 5 pgs.
"European Application Serial No. 18707802,7, Response to Communication pursuant to Rules 161(1) and 162 EPC filed Mar. 30, 2020", 11 pgs.
"European Application Serial No. 06009368.9, Communication Pursuant to Article 94(3) EPC dated Mar. 1, 2017", 5 pgs.
"European Application Serial No. 06009368.9, Communication Pursuant to Article 94(3) EPC dated Oct. 8, 2015", 4 pgs.
"European Application Serial No. 06009368.9, Extended European Search Report dated Sep. 15, 2006", 11 pgs.
"European Application Serial No. 06009368.9, Office Action dated Jun. 14, 2007", 1 pg.
"European Application Serial No. 06009368.9, Response filed Apr. 18, 2016 to Communication Pursuant to Article 94(3) EPC dated Oct. 8, 2015", 15 pgs.
"European Application Serial No. 06009368.9, Response filed Sep. 11, 2017 to Communication Pursuant to Article 94(3) EPC dated Mar. 1, 2017", 24 pgs.
"European Application Serial No. 06009368.9, Response filed Dec. 24, 2007 to Office Action dated Jun. 14, 2007", 11 pgs.
"European Application Serial No. 18706624.6, Response to Communication pursuant to Rules 161(1) and 162 EPC filed May 5, 2020", 11 pgs.
"European Application Serial No. 18707204.6, Response to Communication pursuant to Rules 161(1) and 162 EPC filed Mar. 30, 2020", 17 pgs.
"International Application Serial No. PCT/US2018/017582, International Preliminary Report on Patentability dated Sep. 19, 2019", 9 pgs.
"International Application Serial No. PCT/US2018/017582, International Search Report dated May 16, 2018", 7 pgs.
"International Application Serial No. PCT/US2018/017582, Written Opinion dated May 16, 2018", 7 pgs.
"international Application Serial No. PCT/US2018/017591, International Preliminary Report on Patentability dated Aug. 22, 2019", 11 pgs.
"International Application Serial No. PCT/US2018/017591, International Search Report dated Apr. 25, 2018", 7 pgs.
"International Application Serial No. PCT/US2018/017591, Written Opinion dated Apr. 25, 2018", 9 pgs.
"international Application Serial No. PCT/US2018/017663, International Preliminary Report on Patentability dated Aug. 22, 2019", 18 pgs.
"International Application Serial No. PCT/US2018/017663, International Search Report dated Jun. 18, 2018", 10 pgs.
"International Application Serial No. PCT/US2018/017663, Invitation to Pay Add'l Fees and Partial Search Report dated Apr. 23, 2018", 21 pgs.
"International Application Serial No. PCT/US2018/017663, Written Opinion dated Jun. 18, 2018", 16 pgs.
U.S. Appl. No. 17/034,697, filed Sep. 28, 2020, Pectus Bar and Stabilizer Devices and Methods.
"U.S. Appl. No. 15/893,271, Notice of Allowance dated Jun. 29, 2020", 11 pgs.
"U.S. Appl. No. 16/804,325, Notice of Allowance dated Apr. 27, 2022", 8 pgs.
"U.S. Appl. No. 16/804,325, Notice of Allowance dated Dec. 27, 2021", 11 pgs.
"U.S. Appl. No. 17/034,697 Supplemental Preliminary Amendment Filed Feb. 21, 2022", 6 pgs.
"U.S. Appl. No. 17/034,697, Non Final Office Action dated Apr. 12, 2022", 13 pgs.

(56) References Cited

OTHER PUBLICATIONS

"U.S. Appl. No. 17/034,697, Preliminary Amendment filed Sep. 29, 2020", 6 pgs.
"Australian Application Serial No. 2018230818, Response filed Aug. 28, 2020 to Subsequent Examiners Report dated May 28, 2020", 17 pgs.
"Australian Application Serial No. 2018230818, Response filed Nov. 20, 2020 to Subsequent Examiners Report dated May 28, 2020", 11 pgs.
"Australian Application Serial No. 2018230818, Subsequent Examiners Report dated Sep. 21, 2020", 4 pgs.
"Canadian Application Serial No. 3,053,113, Non Final Office Action dated Apr. 1, 2022", 5 pgs.
"Canadian Application Serial No. 3,053,113, Office Action dated May 31, 2021", 5 pgs.
"Canadian Application Serial No. 3,053,113, Office Action dated Sep. 25, 2020", 4 pgs.
"Canadian Application Serial No. 3,053,113, Response filed Sep. 29, 2021 to Office Action dated May 31, 2021", 20 pgs.
"Canadian Application Serial No. 3,053,113, Response to Office Action dated Sep. 25, 2020", 29 pgs.
"Canadian Application Serial No. 3,054,790, Office Action dated Nov. 12, 2020", 4 pgs.
"Canadian Application Serial No. 3,054,790, Response filed Mar. 12, 2021 to Office Action dated Nov. 12, 2020", 13 pgs.
"Chinese Application Serial No. 201880011148.1, Office Action dated Feb. 14, 2022", w/English Translation, 18 pgs.
"Chinese Application Serial No. 201880011148.1, Response filed Jan. 4, 2022 to Notification of Paying the Restoration Fee dated Nov. 18, 2021", w/ Claims, 6 pgs.
"Chinese Application Serial No. 201880014508.3, Office Action dated Nov. 17, 2021", w/ English translation, 9 pgs.
"Chinese Application Serial No. 201880014508.3, Response filed Feb. 23, 2022 to Office Action dated Nov. 17, 2021", w/ English claims, 10 pgs.
"European Application Serial No. 18707204.6, Communication Pursuant to Article 94(3) EPC dated Mar. 16, 2022", 8 pgs.
"Japanese Application Serial No. 2019-543354, Notification of Reasons for Refusal dated Jan. 5, 2021", (W/ English Translation), 11 pgs.
"Japanese Application Serial No. 2019-543354, Notification of Reasons for Refusal dated Dec. 7, 2021", w/ English translation, 8 pgs.
"Japanese Application Serial No. 2019-543354, Response filed Mar. 7, 2022 to Notification of Reasons for Refusal dated Dec. 7, 2021", w/English Claims, 15 pgs.
"Japanese Application Serial No. 2019-543354, Response filed Jun. 30, 2021 to Notification of Reasons for Refusal dated Jan. 5, 2021", w/ English claims, 13 pgs.
"Japanese Application Serial No. 2019-548548, Notification of Reasons for Refusal dated Jan. 5, 2021", (W/ English Translation), 10 pgs.
"Japanese Application Serial No. 2019-548548, Response filed Apr. 5, 2021 to Notification of Reasons for Refusal dated Jan. 5, 2021", w/ English claims, 10 pgs.

* cited by examiner

STABILIZER HOLDER AND INSERTER TOOL AND METHODS

CLAM OF PRIORITY

This application is a continuation of U.S. patent application Ser. No. 15/892,926, filed on Feb. 9, 2018, which claims the benefit of U.S. Provisional Patent Application Ser. No. 62/457,532, filed on Feb. 10, 2017, and U.S. Provisional Patent Application Ser. No. 62/483,494, filed on Apr. 10, 2017, the benefit of priority of each of which is claimed hereby, and each of which are incorporated by reference herein in its entirety.

BACKGROUND

Pectus excavatum and pectus carinatum are conditions affecting a human rib cage which can result from a congenital disorder or deformity. In some cases of pectus excavatum and pectus carinatum, physicians install hardware into a patient's ribcage to reshape the ribcage. Depending on the anatomy of the patient, current hardware solutions may be difficult to secure to a patient. Further, because some surgical methods attempt to minimize the number and size of surgical incisions, hardware installed on the ribcage may be difficult for a physician to reach and/or secure.

OVERVIEW

In cases where pectus carinatum or pectus excavatum require surgical correction, a common corrective procedure includes securing a pectus bar to a patient's rib cage to reshape and stabilize the rib cage. This procedure can include the steps of: creating opposing incisions on each side of a patient's rib cage; inserting a curved pectus bar into one of the incisions; weaving the pectus bar through one or more ribs; flipping the pectus bar; securing the pectus bar to the rib cage; securing one or more stabilizers to the pectus bar; securing the one or more stabilizers to the rib cage; and, closing the incisions.

In some of these surgical procedures, incisions are located on an outer (lateral) portion of the rib cage for aesthetic purposes. In some of these procedures, stabilizers may be difficult for a physician to position on the pectus bar and the stabilizers may be difficult for a physician to secure to the pectus bar. The inventors have recognized, among other things, that a stabilizer tool can be used to secure a stabilizer to the tool, place the stabilizer on the pectus bar, and engage a lock of the stabilizer to secure the stabilizer to the pectus bar. These methods can simplify and shorten the surgical procedure and help reduce damage to components during the procedure, saving time and cost.

To further illustrate the apparatuses and systems disclosed herein, the following non-limiting examples are provided:

Example 1 is a pectus bar stabilizer insertion tool comprising: a first handle including a first distal portion; a second handle including a second distal portion, the second handle pivotably coupled to the first handle, the first and second handles moveable between an open position and a closed position; a first head coupled to the first distal portion and engageable with a first portion of a stabilizer, the first head including: a driver engageable with a lock of the stabilizer; a second head coupled to the second distal portion and engageable with a second portion of the stabilizer; and a locking shaft extending from the first head, the locking shaft coupled to the driver and operable to lock and unlock the stabilizer to a pectus bar.

In Example 2, the subject matter of Example 1 optionally includes the first head further comprising a snap fitting extending from the first head generally towards the second head, the snap fitting engageable with the stabilizer to secure the stabilizer to the first head.

In Example 3, the subject matter of Example 2 optionally includes the second head further comprising a snap bore alignable with the snap fitting when the first handle and second handle are in the closed position, the snap bore sized to be larger than the snap fitting.

In Example 4, the subject matter of Example 3 optionally includes the stabilizer comprising a first stabilizer bore alignable with the snap bore when the first handle and second handle are in the closed position, and wherein the snap fitting is releasably securable to the first stabilizer bore.

In Example 5, the subject matter of any one or more of Examples 1-4 is optionally configured such that the locking shaft includes a shaft circumferential groove, and the first head further comprises a first pin engaging the shaft circumferential groove to restrict translation of the locking shaft.

In Example 6, the subject matter of any one or more of Examples 1-5 optionally includes the first head further comprising a second pin engaging the driver to restrict translation of the driver.

In Example 7, the subject matter of any one or more of Examples 1-6 optionally includes a locking handle coupled to a proximal end of the locking shaft.

In Example 8, the subject matter of any one or more of Examples 1-7 is optionally configured such that the driver comprises a gear, and the locking shaft comprises a worm drive disposed at a distal end of the locking shaft, the worm drive engageable with the gear to operate the driver.

In Example 9, the subject matter of any one or more of Examples 1-8 is optionally configured such that the first head and the second head are contoured so that the stabilizer recesses into the first head and the second head when the stabilizer engages the first head and the second head.

In Example 10, the subject matter of any one or more of Examples 1-9 is optionally configured such that the second head is contoured so that the pectus bar recesses into the second head when the pectus bar engages the second head.

In Example 11, the subject matter of any one or more of Examples 1-10 optionally includes the first head further comprising a driver bore extending into the first head, the driver disposable in the driver bore.

In Example 12, the subject matter of Example 11 optionally includes the first head further comprising a locking shaft bore extending into the first head from an outer surface of the first head substantially perpendicular to and intersecting the driver bore, allowing the locking shaft to engage the driver.

Example 13 is a pectus bar assembly comprising: a pectus bar insertable into a human rib cage; a stabilizer securable to the pectus bar and to the human rib cage, the stabilizer comprising: a first portion including a locking cam; and a second portion opposite the first portion; and a stabilizer tool comprising: a first handle including a first distal portion; a second handle including a second distal portion, the second handle pivotably coupled to the first handle, the first and second handles moveable between an open position and a closed position; a first head coupled to the first distal portion and engageable with the first portion of the stabilizer, the first head including a driver engageable with the locking cam; a second head coupled to the second distal portion and engageable with the second portion of the stabilizer; and a locking shaft extending from the first head, the locking shaft coupled to the driver to operate the locking cam.

In Example 14, the subject matter of Example 13 optionally includes the first head further comprising a snap fitting extending from the first head generally towards the second head, the snap fitting engageable with the stabilizer to secure the stabilizer to the first head.

In Example 15, the subject matter of Example 14 optionally includes the second head further comprising a snap bore alignable with the snap fitting when the first handle and the second handle are in the closed position, the snap bore sized to be larger than the snap fitting.

In Example 16, the subject matter of any one or more of Examples 13-15 is optionally configured such that the locking shaft includes a shaft circumferential groove, and the first head further comprises a first pin engaging the shaft circumferential groove to restrict translation of the locking shaft.

In Example 17, the subject matter of any one or more of Examples 13-16 optionally includes the first head further comprising a second pin engaging the driver to restrict translation of the driver.

In Example 18, the subject matter of any one or more of Examples 13-17 is optionally configured such that the driver comprises a gear, and the locking shaft further comprises a worm drive disposed at a distal end of the locking shaft, the worm drive engageable with the gear to operate the driver.

Example 19 is a method of securing a stabilizer to a pectus bar, the method comprising: placing a stabilizer over a pectus bar using a stabilizer tool; operating a first handle and a second handle of the stabilizer tool to close a first head and a second head of the stabilizer tool around the pectus bar and the stabilizer, wherein closing the first head and the second head engages a driver of the first head with a locking cam of the stabilizer; and rotating a locking shaft of the stabilizer tool to lock the locking cam to the pectus bar.

In Example 20, the subject matter of Example 19 optionally includes securing the stabilizer to a snap fitting of the first head.

In Example 21, the subject matter of one or more of Examples 19-20 is optionally configured such that the first handle and the second handle are operated from a position outside an incision and the first head and second head are within the incision.

In Example 22, the subject matter of one or more of Examples 19-21 optionally includes positioning the stabilizer on the pectus bar as desired when the first head and second head are closed and when the locking cam is unlocked.

In Example 23, the subject matter of one or more of Examples 19-223 is optionally configured such that closing the first head and the second head causes the first head to engage a body of the stabilizer and the second head to engage the body of the stabilizer and the pectus bar.

In Example 24, the pectus bar stabilizer insertion tool, assembly, or method of any one of or any combination of Examples 1-23 is optionally configured such that all elements or options recited are available to use or select from.

These and other examples and features of the present apparatuses and systems will be set forth in part in the following Detailed Description. This Overview is intended to provide non-limiting examples of the present subject matter and it is not intended to provide an exclusive or exhaustive explanation. The Detailed Description below is included to provide further information about the present apparatuses and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to devices and systems for pectus correction procedures. For example, the present application discloses an assembly for coupling a pectus bar and stabilizers to a rib cage of a patient to correct pectus excavatum and pectus carinatum.

Figure 1:
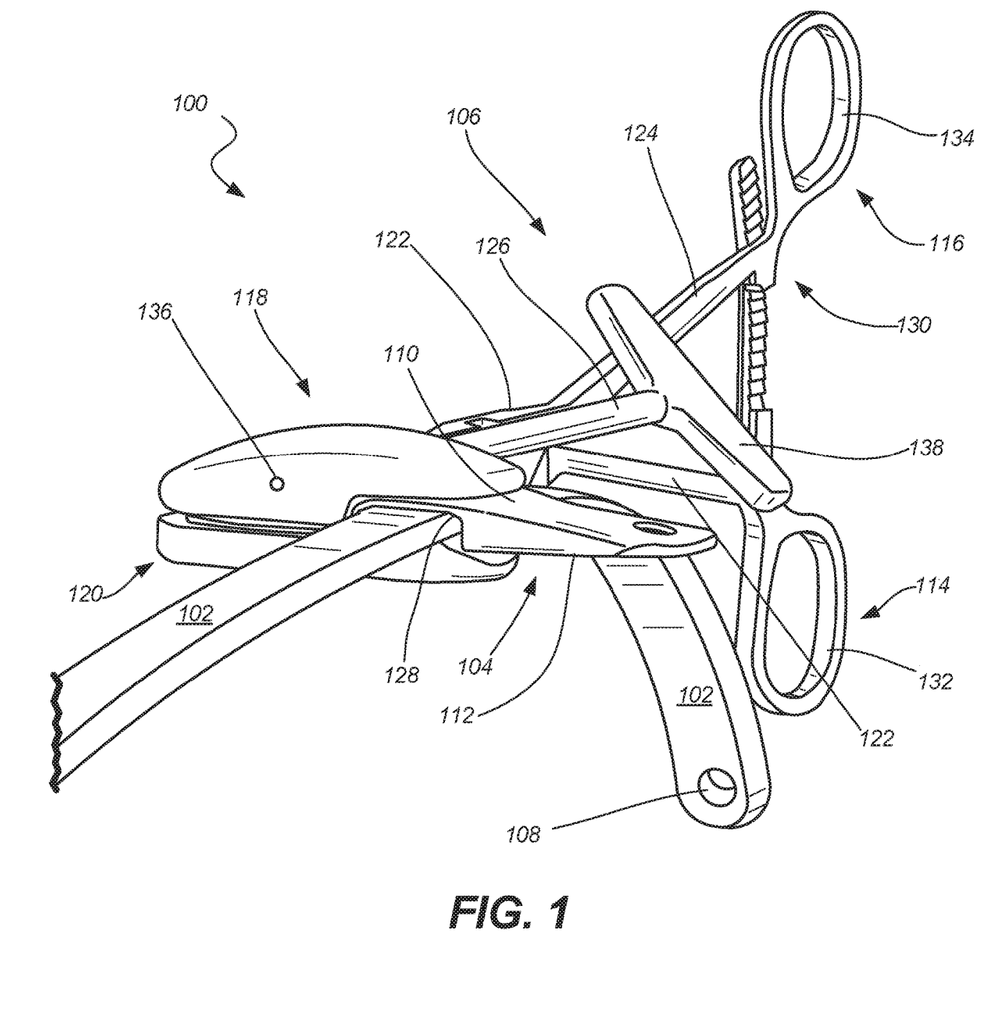
FIG. 1 illustrates an isometric view of a pectus bar assembly, in accordance with at least one example of the present disclosure.

FIG. 1 illustrates an isometric view of pectus bar assembly 100, which can include pectus bar 102, stabilizer 104, and stabilizer tool 106. Pectus bar 102 can include bar bores 108 (only one shown in FIG. 1). Stabilizer 104 can include first portion 110 and second portion 112. Stabilizer tool 106 can include first handle 114, second handle 116, first head 118, second head 120, first arm 122, second arm 124, and locking shaft 126.

Pectus bar 102 can be a rigid or semi-rigid bar constructed of materials such as metals and plastics. Pectus bar 102 can have an elongate body forming a curve, such as a c-shape, in some examples. Bar bores 108 can be disposed near the terminations of pectus bar 102 and can be configured to receive fasteners, such as bone screws or sutures, to secure pectus bar 102 to ribs and/or soft tissues (such as muscles and cartilage) of a patient.

Stabilizer 104 can be a rigid or semi-rigid component constructed of materials such as metals and plastics. Stabilizer 104 can be configured to engage and secure to pectus bar 102 anywhere along the length of pectus bar 102. Stabilizer 104 can also include bores (discussed later) that can be used to secure stabilizer 104 to ribs and/or soft tissues of the patient, Stabilizer 104 can also include a locking mechanism (shown and discussed below) that can be used to secure stabilizer 104 to pectus bar 102. First portion (or first side) 110 of stabilizer 104 can be opposite second portion (or second side) 112.

First handle 114 of stabilizer tool 106 can be coupled to a first end of first arm 122 and first head 118 can be coupled to a second end of first arm 122, Similarly, second handle 116 can be coupled to a first end of second arm 124 and second head 120 can be coupled to a second end of second arm 124. First arm 122 and second arm 124 can be pivotably coupled between first and second handles 114 and 116 and first and second heads 118 and 120, respectively.

In operation of some examples, a procedure to correct pectus excavatum or pectus carinatum can include creating opposing incisions on each side of a patient's rib cage and inserting pectus bar 102 into one of the incisions. Pectus bar 102 can then be weaved through one or more ribs of the patient and flipped into a final position. Thereafter, stabilizers 104 can be inserted into the incisions and secured to pectus bar 102 and to the rib cage of the patient before final preparations are made and incisions are closed. During this process, a physician can position stabilizers 104 along the length of the bar as desired. However, in some procedures, because of the lateral placement of incisions and because of a sometimes desired medial position of stabilizer 104, placement of stabilizer 104 and securing of stabilizer 104 by hand may be difficult. In such cases, stabilizer tool 106 can be used to secure stabilizer 104 to first portion 118 of stabilizer tool 106. Stabilizer 104 and stabilizer tool can then be inserted into an incision and a physician can use first handle 114 and second handle 116 to position stabilizer 104 on pectus bar 102 when first handle 114 and second handle 116 are in an either an open or closed position, as stabilizer 104 is secured to first head 118.

Once stabilizer 104 is positioned on pectus bar 102, first handle 114 and second handle 116 can be moved to a closed position, temporarily securing stabilizer 104 to pectus bar 102. When the physician has positioned stabilizer 104 at a desired location on pectus bar 102 using first handle 114 and second handle 116, the physician can rotate locking shaft 126 to operate the locking mechanism of stabilizer 104, locking stabilizer 104 to pectus bar 102 in the desired position. Stabilizer tool 106 thus enables a physician to place and secure a stabilizer on a pectus bar in a location relative to an incision that may otherwise be difficult to reach. Stabilizer 106 therefore can increase procedural efficiency, which can save time and cost. The details of the components of pectus bar assembly 100 shown in FIG. 1 are discussed in further detail below.

In some examples, stabilizer 104 can include recessed portion 128. Stabilizer tool 106 can include ratchet lock 130. First handle 114 can include finger hole 132 and second handle 116 can include finger hole 134. First head 118 can include driver pin bore 136. Locking shaft 126 can include locking handle 138.

Recessed portion 128 can be a recess that is open at second portion 112 of stabilizer 104. Recessed portion 128 can be sized and shaped to receive pectus bar 102. In some other examples, recessed portion 128 can be open to first portion 110. A locking mechanism (discussed below in FIG. 2) can engage pectus bar 102 at recessed portion 128 to lock stabilizer 104 to pectus bar 102.

Ratchet lock 130 can connect to first arm 122 and second arm 124 proximate first handle 114 and second handle 116, respectively. In operation of some examples, ratchet lock 130 can temporarily fix the position of first handle 114 relative to second handle 116 and therefore first head 118 relative to second head 120, for example in a closed position. Ratchet lock 130 can be released so that first handle 114 and second handle 116 can be moved between open and closed positions.

First head 118 can include driver pin bore 136, which can be used to secure a driver within first head 118, as discussed further below. Locking shaft 126 can include locking handle 138, which can be used to apply a torque to locking shaft 126 in either rotational direction to operate the driver within first head 118, as described further below.

Figure 2:
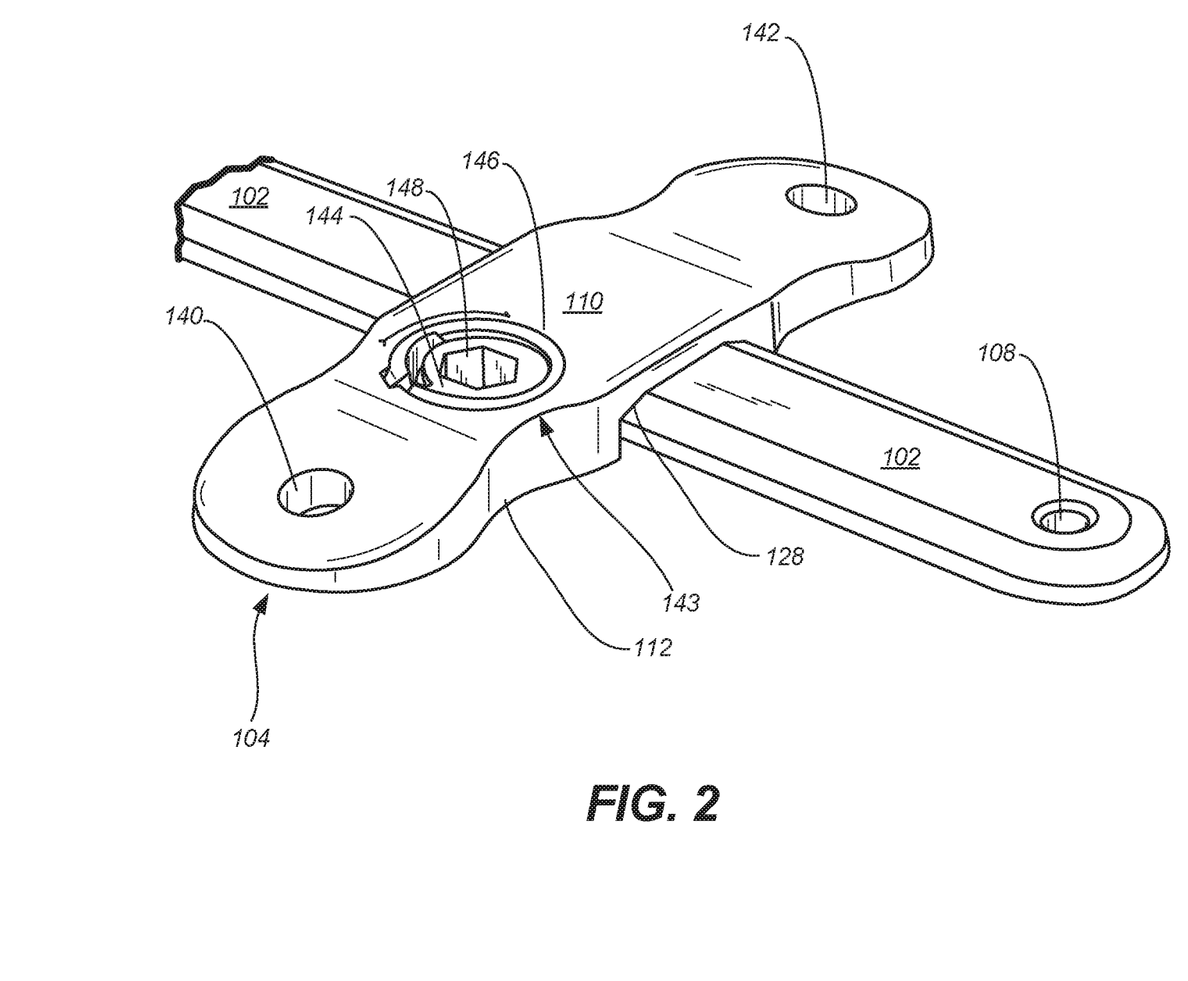
FIG. 2 illustrates an isometric view of a stabilizer and pectus bar, in accordance with at least one example of the present disclosure.

FIG. 2 illustrates an isometric view of pectus bar 102 and stabilizer 104 of pectus bar assembly 100. Pectus bar 102 can include bar bores 108 (one shown in FIG. 2). Stabilizer 104 can include first portion 110, second portion 112 (not clearly visible in FIG. 2), recessed portion 128, stabilizer bores 140 and 142, and lock 143, which can include locking cam 144, cam bore 146, and tool engagement 148.

The components illustrated in FIG. 1 can be connected and can operate consistently with FIG. 1; however, FIG. 2 shows additional details of pectus bar 102 and stabilizer 104. For example, FIG. 2 shows stabilizer bores 142, which can be used to secure stabilizer 104 to bones, such as ribs, or soft tissues of a patient. Stabilizer bores 142 can be configured to receive fasteners, such as bone screws or sutures, in some examples.

FIG. 2 also shows lock 143 of stabilizer 104, which can be a lock that is operable to secure stabilizer 104 to pectus bar 102 at recessed portion 128. More specifically, cam bore 146 can be a bore extending from first portion 110 into stabilizer 104 and intersecting recessed portion 128. Cam bore 146 can include a captivated or integral slot that engages an integral tab of locking cam 144. Cam 144 can be a rotatable member configured to receive a driver at tool engagement 148. Tool engagement 148 can be configured to receive many types of drivers, such as slotted, cross-recess, hex, star, and the like. Cam 144 can include a tab engageable with bore 146, and can include a portion that engages pectus bar 102 to secure stabilizer 104 thereto. In some examples the tab and its engagement with bore 146 can prevent passive rotation of cam 144 and/or unlocking.

In operation of some examples, stabilizer 104 can be placed and positioned on pectus bar 102 so that recessed portion 128 engages pectus bar 102. A driver, such as a driver of stabilizer tool 106, as described below, can be inserted into tool engagement 148 and the driver can be rotated (for example in a clock-wise direction) to rotate locking cam 144 to lock against bore 146 and lock stabilizer 104 to pectus bar 102. This process can be reversed by rotating the driver in the opposite direction (for example, in a counter-clock-wise direction) to rotate locking cam 144, which can disengage locking cam 144 from locking bore 146 and pectus bar 102, so that stabilizer 104 can be removed from pectus bar 102 or can be repositioned relative to pectus bar 102. Though FIG. 2 shows only one type of locking cam and locking bore, stabilizer tool 106 can be used to drive many types of cams or fasteners.

Figure 3:
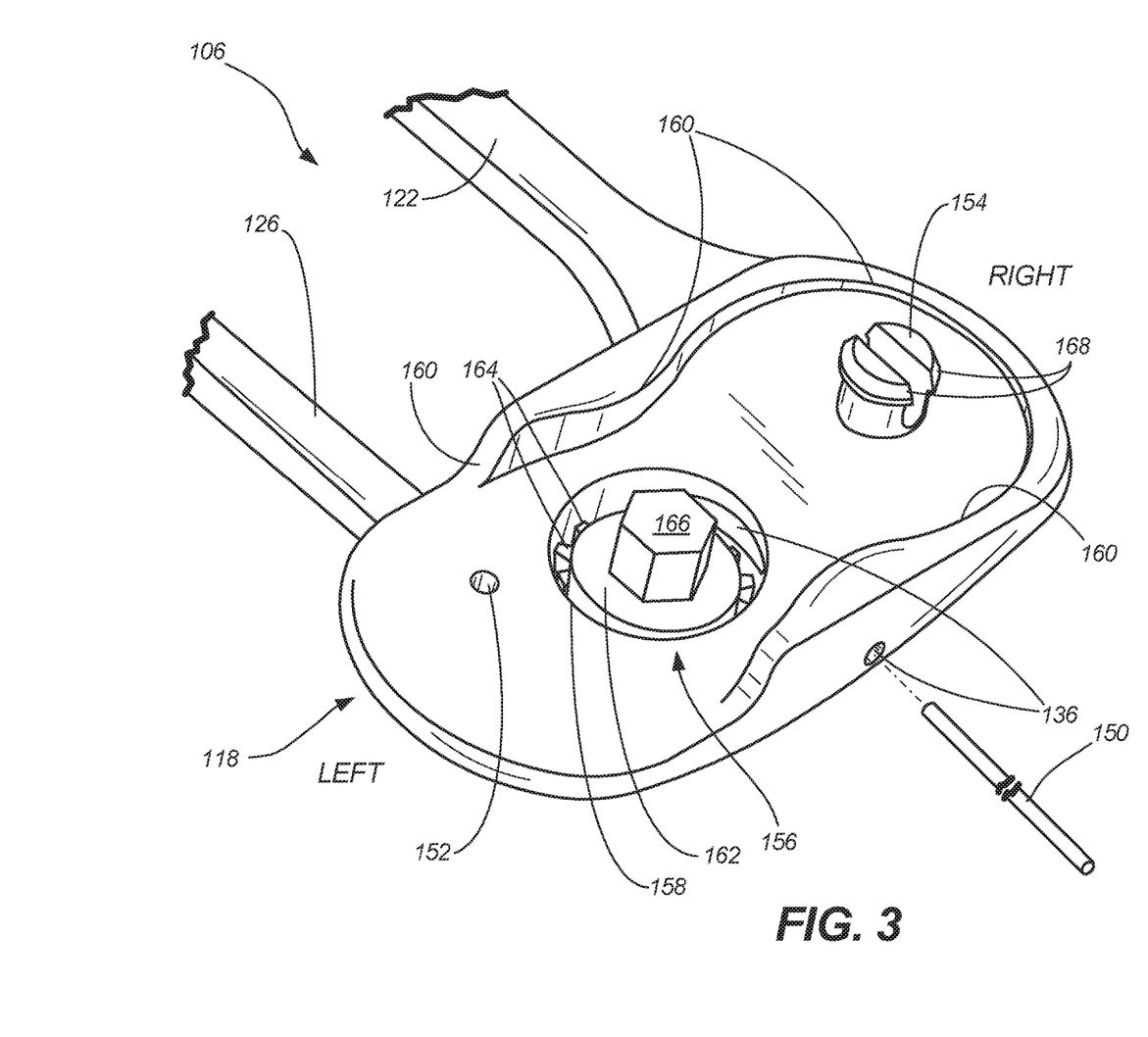
FIG. 3 illustrates an isometric view of a portion of a stabilizer tool, in accordance with at least one example of the present disclosure.

FIG. 3 illustrates an isometric view of a portion of stabilizer tool 106, which can include first head 118, first arm 122, and locking arm 126. First head 118 can include driver pin bore 136, driver pin 150, shaft pin bore 152, snap fitting 154, driver 156, driver bore 158, and contouring 160. Driver 156 can include driver gear 162 (including teeth 164) and driver bit 166. Snap fitting 154 can include projections 168. Also shown in FIG. 3 are orientation indicators Left and Right. The components of FIG. 3 can connect and operate consistently with the components of FIGS. 1 and 2; however, FIG. 3 shows additional details of stabilizer tool 106.

First arm 122 can connect to a right portion of first head 118 and locking shaft 126 can enter first head 118 at a left portion of first head 118. Locking shaft 126 can terminate within the left portion of first head 118, and can engage driver 156 within first head 118, as described further below.

Driver pin 150 can be a pin, having a shape such as a cylinder, or other prismatic shape, and can be comprised of a rigid material, such as plastics, metals, and the like. Driver pin 150 can extend through first head 118, passing through driver pin bore 136 at a medial location of first head 118

(between left and right portions of first head 118). Driver pin bore 136 can pass over driver 156, so that driver pin 150 can engage driver 156, restricting axial motion of driver 156, while driver bore restricts motion of driver 156 in other directions.

Shaft pin bore 1152 can be a bore extending through the left portion of first head 118, proximate a termination of locking shaft 126 (as discussed further below).

Snap fitting 154 extends from a surface of a right portion of first head 118 (generally towards second head 120 of FIG. 1). Though only one snap fitting is shown in FIG. 3, more snap fittings, such as 1, 3, 4, 5, 10, and the like can be used. Snap fitting 154 includes two prongs, each having a projection 164 extending radially from each prong of snap fitting 154. Projections 168 can have a radius or diameter that is larger than that of a portion of the prongs connecting to first head 118.

The prongs of snap fitting 154 are shown as being separated by a gap or slot, so that any force transverse to an axis of the snap fitting can cause one or both of the prongs to breach the gap, reducing the total diameter of snap fitting 154. When the diameter of snap fitting 154 is reduced, snap fitting 154 can be inserted into a bore having a diameter smaller than that of projections 168 when snap fitting 154 is uncompressed. Projections 168 can expand to their normal diameter when projections 168 clear the bore, such as one of stabilizer bores 140 and 142 of FIG. 2. In the same way, when the prongs or projections 168 are compressed, snap fitting can disengage from a bore.

Driver 156 can be disposed in a bore of first head 118, such as driver bore 158. Driver bore 158 can be circular in some examples, and can be of other shapes, such as octagonal, in other examples. Driver bore 158 can be sized to allow driver 156 to rotate within driver bore 158 without impeding the rotation of driver 156, while limiting substantial non-rotational movement of driver 156 relative to driver bore 158.

Figure 5:
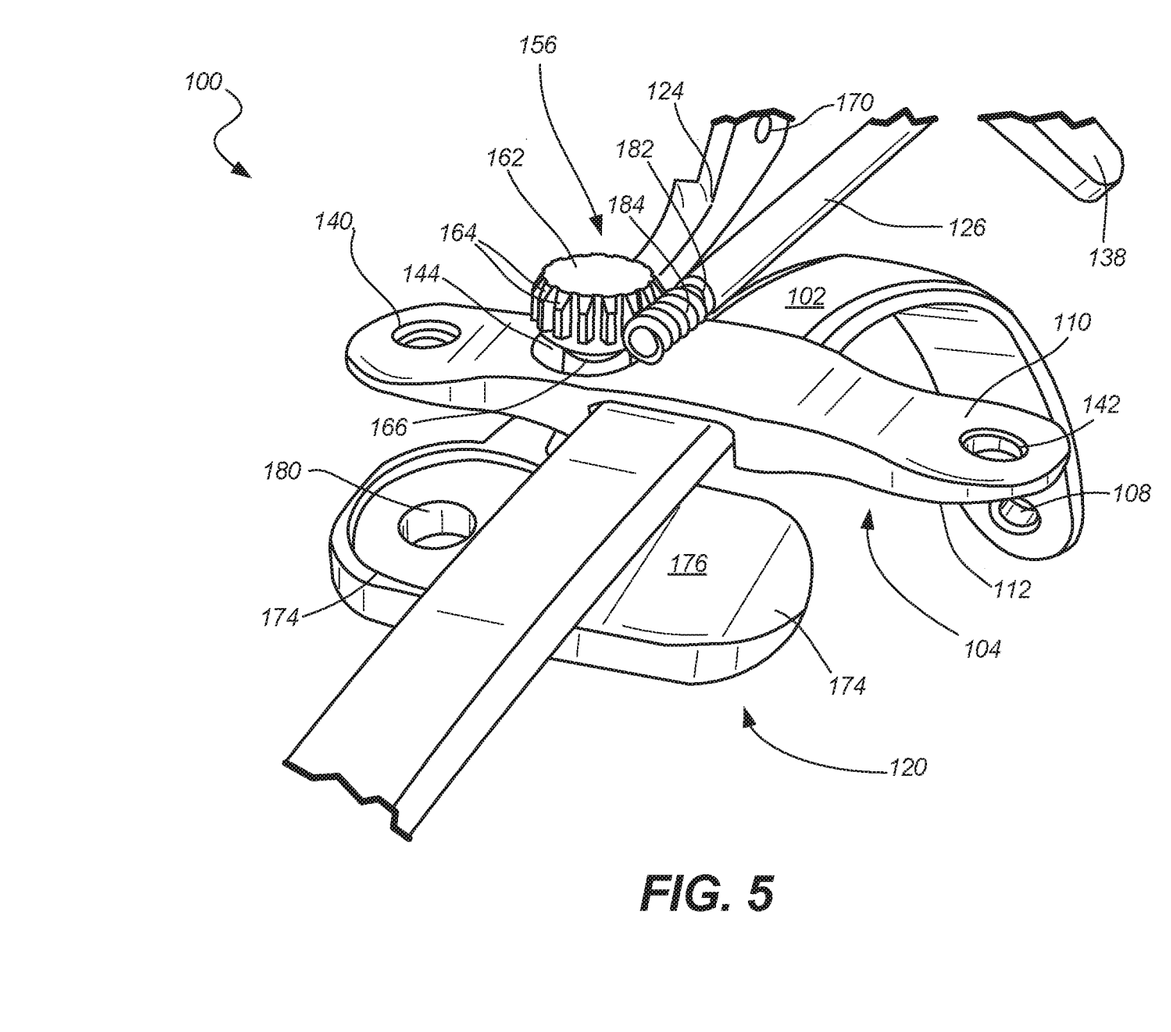
FIG. 5 illustrates a partially exploded isometric view of a pectus bar assembly, in accordance with at least one example of the present disclosure.

Driver 156 can include driver gear 162, which can be a parallel axis gear, such as a spur gear, in some examples. Driver gear 162 can interface with a gear of locking shaft 126 at teeth 164 of driver gear 162, as shown in FIG. 5 below, Driver bit 166 can extend from a non-geared surface of driver gear 162 and can protrude from driver bore. The interaction between driver gear 162 and locking shaft 126 is discussed below in further detail in FIG. 5.

First head 118 can include head contouring 160, which can be a perimeter wall that is shaped to receive, or interface with, a stabilizer, such as stabilizer 104 of FIGS. 1 and 2. Contouring 160 can be designed so that stabilizer 104 nests within first head 118 to limit movement of stabilizer 104 relative to first head 118 when stabilizer 104 is secured by snap fitting 154 and/or driver 156, as discussed further below.

In operation of some examples, snap fitting 154 can be used to secure a stabilizer, such as stabilizer 104 of FIGS. 1 and 2, to first head 118. That is, snap fitting 154 of first head 118 can be aligned with a bore of stabilizer 104, such as bores 140 or 142 of FIG. 2. A force can then be applied to first head 118 (for example using first handle 114) and stabilizer 104 so that the walls or edges of the bore apply a force to projections 168, compressing the prongs of snap fitting 154, reducing the diameter of snap fitting 154, and allowing snap fitting 154 to enter the bore. When projections 168 have passed through the bore, projections 168 can expand, securing stabilizer 104 to stabilizer tool 106. In this position, stabilizer 104 can be nested within contouring 160 of head 118, further securing stabilizer 104 to first head 118.

Once stabilizer 104 is coupled to stabilizer tool 106, stabilizer tool 106 can be used to position stabilizer 104 on pectus bar 102. In another example, stabilizer 104 can be placed on pectus bar 102 before securing stabilizer 104 to stabilizer tool 106. In either case, after coupling stabilizer tool 106 to stabilizer 104, stabilizer tool 106 can be closed using first handle 114 and second handle 116, securing stabilizer 104 to pectus bar 102, without locking the position of stabilizer 104 relative to pectus bar 102. Stabilizer 104 can then be positioned at any desired location on pectus bar 102 without losing an interface between stabilizer 104 and pectus bar 102.

When stabilizer tool 106 is in a closed position, driver 156, and more specifically, driver bit 166, can engage tool engagement portion 148 of locking cam 144 (as shown in FIG. 5 below), When stabilizer tool is in this position, locking shaft 126 can be rotated to rotate driver bit 166 in either direction. Rotating driver bit 166 in a clock-wise direction, in some examples, can lock cam lock 144 to pectus bar 102, securing stabilizer 104 to pectus bar 102. Once stabilizer 104 is locked to pectus bar 102, first handle 114 and second handle 116 can be opened, forcing projections 168 to engage an outside portion of one of stabilizer bores 140 and 142, forcing projections 168 inward, compressing snap fitting 154 so that snap fitting 154 can pass through the bore and stabilizer tool 106 can be entirely disengaged from stabilizer 104 and removed from the patient. In this way, stabilizer tool 106 allows a physician to install a stabilizer in positions that may otherwise be difficult to reach or difficult or undesirable to place by hand. Stabilizer tool 106 also allows for positioning or repositioning of stabilizer 104 onto a pectus bar from a position outside an incision. Because stabilizer tool 106 provides a single device for securing, placing, and locking a stabilizer to a pectus bar, stabilizer tool can increase procedural efficiency, saving time and cost.

Figure 4:
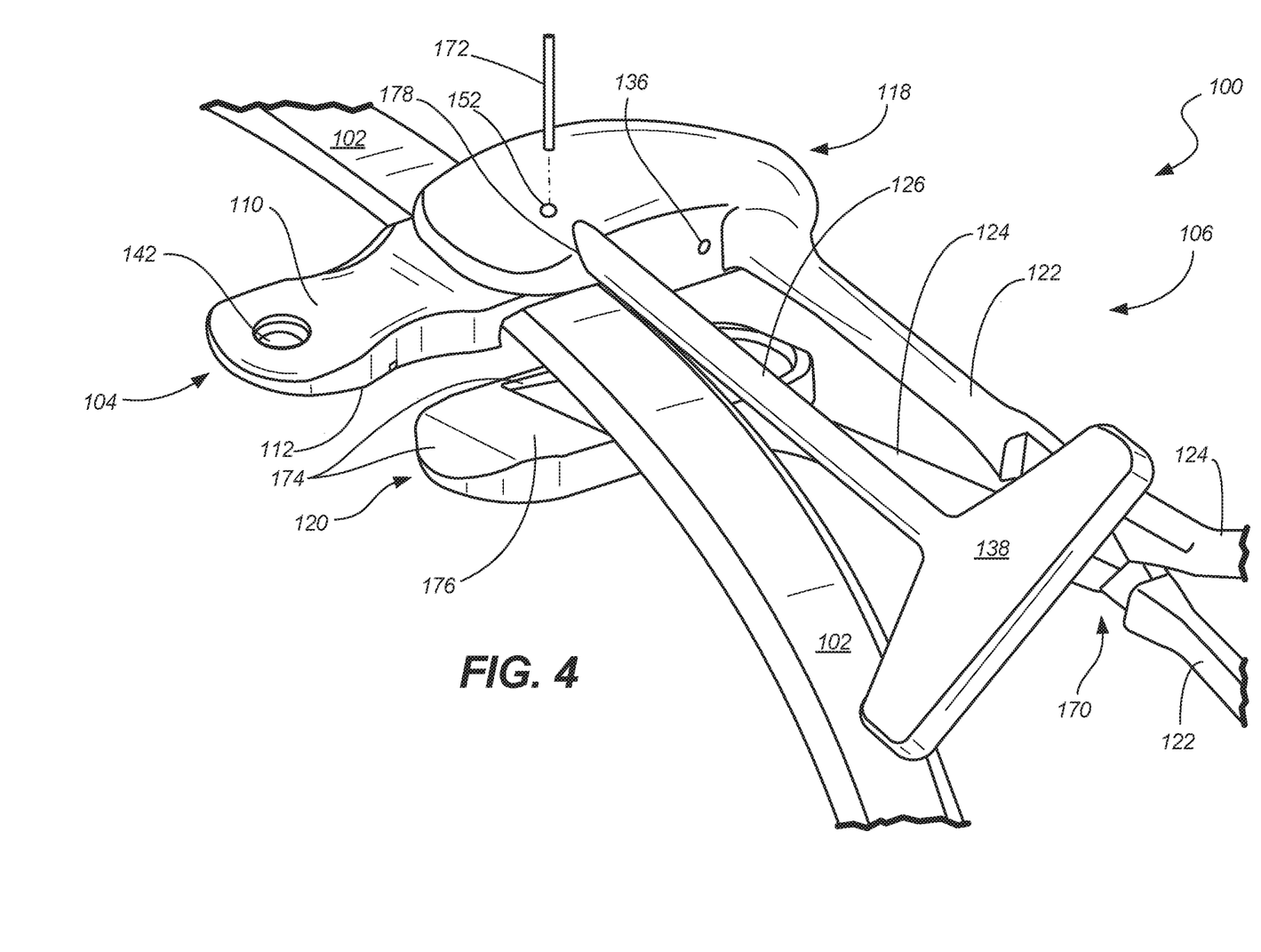
FIG. 4 illustrates an isometric view of a pectus bar assembly, in accordance with at least one example of the present disclosure.

FIG. 4 illustrates an isometric view of pectus bar assembly 100, which can include pectus bar 102, stabilizer 104, and stabilizer tool 106. Stabilizer 104 can include first portion 110, second portion 112, and stabilizer bore 142. Stabilizer tool 106 can include first handle 114, second handle 116, first head 118, second head 120, first arm 122, second arm 124, locking shaft 126, and joint 170. First head 118 can include driver pin bore 136, shaft pin bore 152, shaft pin 172, and locking shaft bore 178. Second head 120 can include contouring 174 and bar engagement portion 176. Locking shaft 126 can include locking handle 138. The components of FIG. 4 can connect and operate consistently with the components of FIGS. 1-3; however, FIG. 4 shows additional details of stabilizer tool 106.

Joint 170 can be a revolute or hinged joint between first arm 122 and second arm 124, in some examples, to form a cross-link or scissor linkage between first arm 122 and second arm 124. This cross-link between first arm 122 and second arm 124 can enable handles 114 and 116 (of FIG. 1) to open and close first head 118 and 120.

Shaft pin 172 can be a pin, having a shape such as a cylinder, or other prismatic shape, and can be comprised of a rigid material, such as plastics, metals, and the like. Shaft pin 172 can extend into first head 118, passing through shaft pin bore 152 near the entrance of locking shaft 126 and into first head 118. Shaft pin bore 152 can pass over locking shaft 126, so that shaft pin 172 can engage locking shaft 126, restricting axial translation locking shaft 126, while locking shaft bore 178 can restrict motion of driver 156 in other directions. Locking shaft bore 178 can be perpendicular to driver bore 148, extending from an outer portion of first head 118 and extending into first head 118 to intersect with driver bore 148.

Second head 120 can include head contouring 174, which can be a perimeter wall or recess that is shaped to receive, or interface with, a stabilizer, such as stabilizer 104. Contouring 174 can be designed so that stabilizer 104 nests within second head 120 to limit movement of stabilizer 104 relative to second head 120 when first head 118 and second head 120 are in a closed position.

Second head 120 can also include bar engagement portion 176, which can be a portion of second head 120 configured to engage pectus bar 102 without restricting motion of second head 120 and therefore stabilizer tool 106 relative to pectus bar 102 when first head 118 and second head 120 are in a closed position.

FIG. 5 illustrates a partially exploded isometric view of pectus bar assembly 100. In FIG. 5, first head 118 is removed to more clearly show how some components of pectus bar assembly 102 connect and operate.

Pectus bar assembly 100 can include pectus bar 102, stabilizer 104, and stabilizer tool 106. Stabilizer 104 can include first portion 110, second portion 112, stabilizer bores 140 and 142, and locking cam 144. Stabilizer tool 106 can include second head 120, second arm 124, locking shaft 126, and joint 170. Second head 120 can include contouring 174, bar engagement portion 176, and snap bore 180. Locking shaft 126 can include locking handle 138, pin groove 182, and worm gear 184. Driver 156 can include driver gear 162 (including teeth 164) and driver bit 166. The components of FIG. 5 can connect and operate consistently with the components of FIGS. 1-4; however, FIG. 5 shows additional details of stabilizer tool 106.

Snap bore 180 can extend through second head 120. Snap bore 180 can be sized to be of a larger diameter than snap fitting 154 (FIG. 3), including projections 168, so that snap fitting 154 can reside within snap bore 180 without applying pressure on either of projections 168, allowing second head 120 to enclose stabilizer 104 without interfering with snap fitting 154.

Pin groove 182 can be a circumferential groove in locking shaft 126 proximate a distal end of locking shaft 126 and adjacent to worm gear 184. In some examples, pin groove 182 can be other types of retention devices, such as a snap ring. Pin groove 182 can be sized to engage shaft pin 172 such that shaft pin 172 prevents axial translation of locking shaft 126, but does not restrict rotation of locking shaft 126.

Worm gear 184 can be disposed at a distal termination of locking shaft 126, in some examples, and at other locations along locking shaft 126 in other examples. Worm gear 184 can be integral to locking shaft 126 in some examples, and can be attached to locking shaft 126 (for example by welding or fastening), in some other examples. Worm gear 184 can be configured to interface with drive gear 162, and more specifically teeth 164 of drive gear 162, in some examples. In some other examples, different types of gears, such as a helical gear, can be used in place of worm gear 184.

In operation of some examples, driver bit 166 is insertable into locking cam 144, as shown in FIG. 5. When driver bit 166 engages locking cam 144, locking shaft 126 (such as locking handle 138) can be rotated, which in turn rotates worm gear 184. Because worm gear 184 interfaces with teeth 164 of driver gear 162, rotation of worm gear 184 causes rotation of driver gear 162 and therefore driver bit 166. That is, by rotating handle 138 of locking shaft 126, driver bit 166 is rotated, and can therefore be used to rotate locking cam 144, in either rotational direction, to lock and unlock locking cam 144 to and from, respectively, pectus bar 102.

Figure 6:
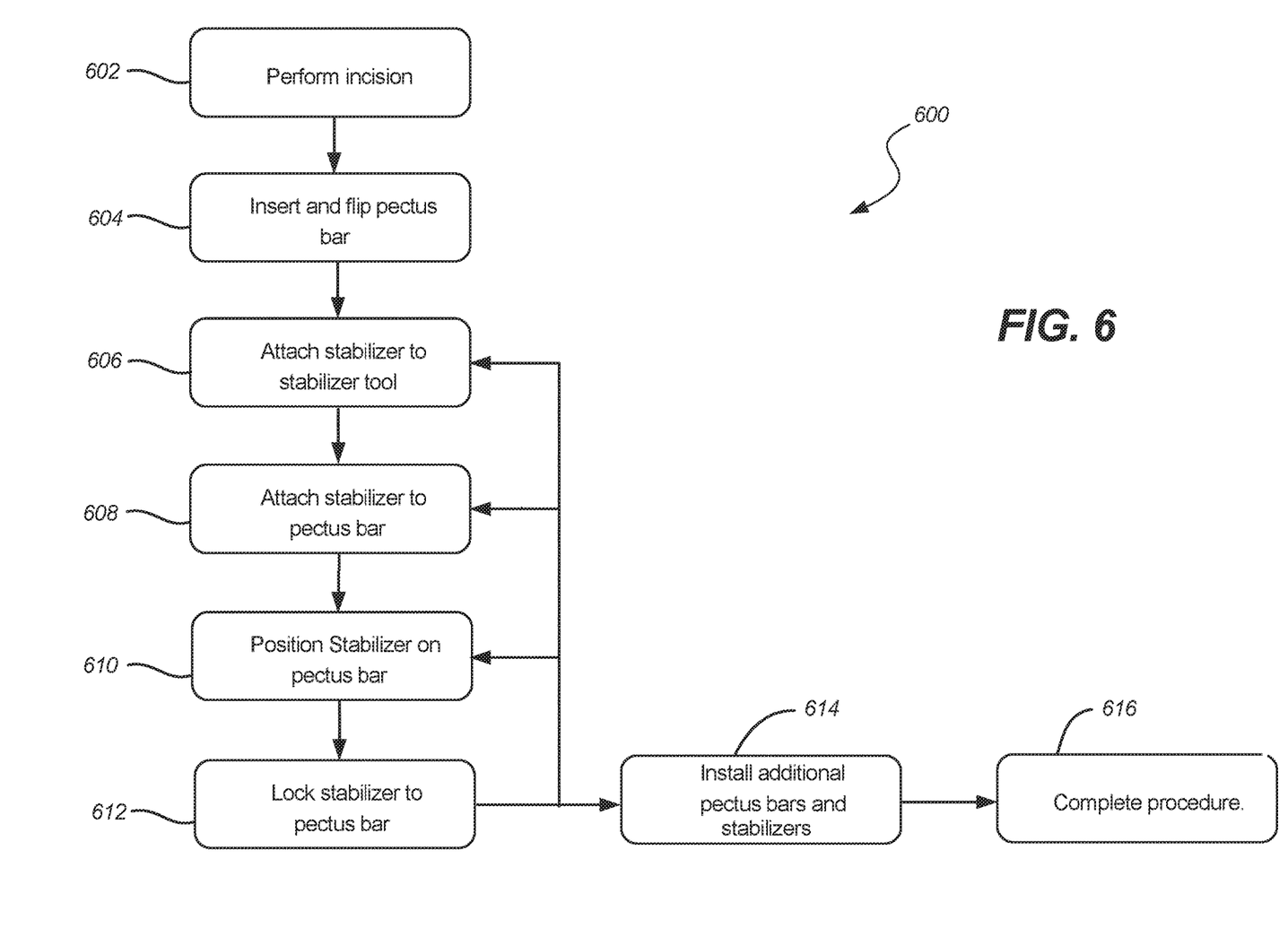
FIG. 6 illustrates a schematic of a method, in accordance with at least one example of the present disclosure.

FIG. 6 shows a flow chart of using the devices and systems described above, in accordance with at least one example of this disclosure. The steps or operations of the method of FIG. 6 are illustrated in a particular order for convenience and clarity. Many of the discussed operations can be performed in a different sequence or in parallel, and some operations may be excluded, without materially impacting other operations. The method of FIG. 6, as discussed, includes operations that may be performed by multiple different actors, devices, and/or systems. It is understood that subsets of the operations discussed in the method of FIG. 6 that are attributable to a single actor, device, or system could be considered a separate standalone process or method.

In operation of one example, a physician can create one or more incisions on a ribcage of a patient at step 602. Other preparations can be made at step 602, such as detachment of soft tissues and resection of ribs, in some examples. At step 604, a pectus bar, such as pectus bar 102, can be inserted into the ribcage and woven through one or more ribs and/or cartilage of the patient. Once fully inserted, the pectus bar can be flipped into an orientation that supports a proper rib cage shape or configuration. At any point after step 604 and prior to step 616, the pectus bar can be directly secured to the patient's rib cage using sutures and/or fasteners, as necessary, passing through a bore of the pectus bar.

At step 606, a stabilizer, such as stabilizer 104 of FIG. 2, can be attached to a stabilizer tool, such as stabilizer tool 106 of FIG. 1. Specifically, a snap fitting of the stabilizer can engage a bore of the stabilizer to secure the stabilizer to the stabilizer tool. The stabilizer may also be supported by contouring of a head of the stabilizer tool, such as contouring 160 of FIG. 3. In some examples, the stabilizer can be attached to the pectus bar prior to attaching the stabilizer to the stabilizer tool.

At step 608, the stabilizer tool can be used to attach the stabilizer to the pectus bar and then positioned relative to the pectus bar at step 610. The stabilizer tool can then be used to lock a locking cam of the stabilizer to the pectus bar at step 612. Following step 612, if necessary, the stabilizer tool can be used to unlock the stabilizer and the stabilizer can be repositioned on the pectus bar. Accordingly steps 606 through 612 can be repeated as necessary to lock the stabilizer to the pectus bar in the desired location.

Once the stabilizer is locked to the pectus bar at a desired location, additional stabilizers can be installed and secured to the pectus bar at step 614. Also, if necessary, additional pectus bars can be installed at step 614, where each bar can receive zero, one, or more stabilizers. The additional stabilizers and/or pectus bars can be installed using any or all of steps 602-612.

After a desired quantity of pectus bars and stabilizers have been installed, the procedure can be completed at step 616, which can include connecting soft tissues, such as muscles, ligaments, cartilage, tendons to bones and to each other, and can include closing the incision or incisions.

Additional Notes

The above detailed description includes references to the accompanying drawings, which form a part of the detailed description. The drawings show, by way of illustration, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more," In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein," Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The invention claimed is:

1. A pectus bar stabilizer insertion tool for securing a stabilizer to a pectus bar, the insertion tool comprising:
   a first handle including a first distal portion;
   a second handle including a second distal portion; the second handle pivotably coupled to the first handle, the first and second handles moveable between an open position and a closed position;
   a first head coupled to the first distal portion and engageable with a first portion of the stabilizer, the first head including a driver engageable with a lock of the stabilizer;
   a second head coupled to the second distal portion and engageable with a second portion of the stabilizer; and
   a locking shaft extending from the head, the locking shaft coupled to the driver and configured to operate the driver with respect to the first head and the second head to lock and unlock the stabilizer to the pectus bar.

2. The insertion tool of claim 1, wherein the first head further includes a snap fitting extending from the first head generally towards the second head, the snap fitting engageable with the stabilizer to secure the stabilizer to the first head.

3. The insertion tool of claim 1, wherein the driver includes a gear, and wherein the locking shaft includes a worm drive, the worm drive engageable with the gear to operate the driver.

4. The insertion tool of claim 1, wherein the locking shaft includes a groove and wherein the tool includes a first pin engaging the groove to limit translation of the locking shaft.

5. The insertion tool of claim 4, wherein the first head further includes a second pin engaging the driver to restrict translation of the driver.

6. The insertion tool of claim 4, wherein the second head includes a snap bore alignable with the snap fitting of the first head when the first handle and the second handle are in the closed position.

7. The insertion tool of claim 6, wherein the stabilizer includes a first stabilizer bore alignable with the snap bore when the first handle and the second handle are in the closed position, and wherein the snap fitting is releasably securable to the first stabilizer bore.

8. A pectus bar stabilizer insertion tool for securing a stabilizer to a pectus bar, the insertion tool comprising:
   a first handle and a second handle pivotal coupled to the first handle, the first and second handles moveable between an open position and a closed position;
   a first head coupled to the first handle and engageable with a first portion of the stabilizer, the first head including a driver engageable with a lock of the stabilizer;
   a second head coupled to the second handle and engageable with a second portion of the stabilizer, the first and second heads movable with the first and second handles to secure the stabilizer between the first and second heads when the first and second handles are in the closed position; and
   a locking shaft extending from the first head, the locking shaft coupled to the driver and operable to operate the driver to lock and unlock the stabilizer to the pectus bar.

9. The insertion tool of claim 8, wherein the first head and the second head are contoured so that the stabilizer is configured to recess into the first head and the second head when the stabilizer engages the first head and the second head.

10. The insertion tool of claim 8, wherein the second head is contoured so that the pectus bar is configured to recess into the second head when the pectus bar engages the second head.

11. The insertion tool of claim 8, wherein the first head further includes a driver bore extending into the first head, and wherein the driver is disposable in the driver bore.

12. The insertion tool of claim 11, wherein the first head includes a locking shaft bore extending into the first head from an outer surface of the first head substantially perpendicular to and intersecting the driver bore, allowing the locking shaft to engage the driver.

13. The insertion tool of claim 12, wherein:
   the locking shaft includes a shaft circumferential groove; and
   the first head further comprising a first pin engaging the shaft circumferential groove to restrict translation of the locking shaft.

14. The insertion tool of claim 13, the first head further comprising:
a second pin engaging the driver to restrict translation of the driver.

15. A pectus bar stabilizer insertion tool for securing a stabilizer to a pectus bar, the insertion tool comprising:
a first handle;
a second handle pivotably coupled to the first handle, the first and second handles moveable between an open position and a closed position;
a first head coupled to the first handle and engageable with a first portion of the stabilizer, the first head including a driver engageable with a rotating lock of the stabilizer;
a second head coupled to the second handle and engageable with a second portion of the stabilizer; and
a locking shaft extending from the first head, the locking shaft coupled to the driver and operable to rotate the lock to lock and unlock the stabilizer.

16. The insertion tool of claim 15, wherein the locking shaft includes a shaft circumferential groove, and wherein the tool includes a first pin engaging the shaft circumferential groove to limit translation of the locking shaft.

17. The insertion tool of claim 16, wherein the first head further includes a second pin engaging the driver to restrict translation of the driver, wherein the driver includes a gear, and wherein the locking shaft includes a worm drive located at a distal end of the locking shaft, the worm drive engageable with the gear to operate the driver.

18. The insertion tool of claim 15, wherein the first head further includes a snap fitting extending from the first head generally towards the second head, the snap fitting engageable with the stabilizer to secure the stabilizer to the first head.

19. The insertion tool of claim 18, wherein the second head includes a snap bore alignable with the snap fitting of the first head when the first handle and the second handle are in the closed position.

20. The insertion tool of claim 19, wherein the stabilizer includes a first stabilizer bore alignable with the snap bore when the first handle and the second handle are in the closed position, and wherein the snap fitting is releasably securable to the first stabilizer bore.

* * * * *

UNITED STATES PATENT AND TRADEMARK OFFICE
CERTIFICATE OF CORRECTION

PATENT NO. : 11,432,858 B2
APPLICATION NO. : 16/908188
DATED : September 6, 2022
INVENTOR(S) : Balzano et al.

It is certified that error appears in the above-identified patent and that said Letters Patent is hereby corrected as shown below:

On the Title Page

On page 3, in Column 2, under Item (56) "Other Publications", Line 45, delete ""international" and insert --"International-- therefor On page 3, in Column 2, under Item (56) "Other Publications", Line 52, delete ""international" and insert --"International-- therefor In the Claims In Column 11, Line 56, in Claim 1, delete "portion;" and insert --portion,-- therefor In Column 11, Line 66, in Claim 1, after "from the", insert --first--

In Column 12, Line 30, in Claim 8, delete "pivotal" and insert --pivotably-- therefor Signed and Sealed this
Fourteenth Day of May, 2024

Katherine Kelly Vidal
*Director of the United States Patent and Trademark Office*